United States Patent
Olson

(10) Patent No.: US 10,245,186 B2
(45) Date of Patent: Apr. 2, 2019

(54) MULTI-LAYER DRESSINGS, SYSTEMS, AND METHODS FOR APPLYING REDUCED PRESSURE AT A TISSUE SITE

(71) Applicant: KCI Licensing, Inc., San Antonio, TX (US)

(72) Inventor: Jonathan Scott Olson, Houston, TX (US)

(73) Assignee: KCI Licensing, Inc., San Antonio, TX (US)

( * ) Notice: Subject to any disclaimer, the term of this patent is extended or adjusted under 35 U.S.C. 154(b) by 892 days.

(21) Appl. No.: 13/849,103

(22) Filed: Mar. 22, 2013

(65) Prior Publication Data

US 2013/0218110 A1 Aug. 22, 2013

Related U.S. Application Data

(63) Continuation of application No. 12/560,777, filed on Sep. 16, 2009, now Pat. No. 8,425,478.

(Continued)

(51) Int. Cl.
*A61M 1/00* (2006.01)
*A61F 13/02* (2006.01)
(Continued)

(52) U.S. Cl.
CPC .... *A61F 13/0206* (2013.01); *A61F 13/00068* (2013.01); *A61F 13/00987* (2013.01);
(Continued)

(58) Field of Classification Search
CPC . A61M 1/00; A61M 27/00; A61F 5/44; A61F 13/0206; A61F 13/00068;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Andrew J Mensh

(57) ABSTRACT

The illustrative systems, methods, and dressings for applying reduced pressure to a tissue site are presented that involve quickly removing fluids from the tissue site to reduce or avoid maceration of the epidermis. One dressing includes a dressing material for transferring the reduced pressure to the tissue site and a drape covering at least a portion of the dressing material. The dressing material includes a hydrophobic tissue-interface layer adapted to contact the tissue site. The dressing material also includes a manifold adapted to distribute reduced pressure. The manifold may be a hydrophobic layer. The dressing material also includes one or more absorbent layers adapted to absorb liquid from the tissue site via the tissue-interface layer and the manifold. Other aspects are disclosed.

32 Claims, 3 Drawing Sheets

Related U.S. Application Data

(60) Provisional application No. 61/098,000, filed on Sep. 18, 2008, provisional application No. 61/098,015, filed on Sep. 18, 2008.

(51) Int. Cl.
  *A61F 13/00* (2006.01)
  *A61M 27/00* (2006.01)
  *A61M 35/00* (2006.01)

(52) U.S. Cl.
  CPC ............ *A61F 13/02* (2013.01); *A61F 13/022* (2013.01); *A61F 13/0216* (2013.01); *A61M 1/0088* (2013.01); *A61M 27/00* (2013.01); A61F 2013/00174 (2013.01); A61F 2013/00217 (2013.01); A61F 2013/00246 (2013.01); A61F 2013/00412 (2013.01); A61F 2013/00536 (2013.01); A61F 2013/00885 (2013.01); A61F 2013/00914 (2013.01)

(58) Field of Classification Search
  CPC ............... A61F 13/00987; A61F 13/02; A61F 13/0216; A61F 13/022; A61F 2013/00174; A61F 2013/00217; A61F 2013/00246; A61F 2013/00412; A61F 2013/00536; A61F 2013/00885; A61F 2013/00914; A61B 5/20
  USPC ........................................................ 604/313
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A * | 5/1987 | Webster ............ A61F 13/00021 602/47 |
| 4,710,165 A | 12/1987 | McNeil et al. |
| 4,718,907 A * | 1/1988 | Karwoski ................. A61F 2/06 204/169 |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A * | 6/2000 | Zamierowski ...... A61F 13/0203 604/289 |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |

(56) References Cited

U.S. PATENT DOCUMENTS

| | | |
|---|---|---|
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0161346 A1 | 10/2002 | Lockwood et al. |
| 2004/0030304 A1* | 2/2004 | Hunt ............ A61M 1/0088 604/317 |
| 2004/0073151 A1 | 4/2004 | Weston |
| 2004/0243041 A1* | 12/2004 | Qin ............ A61F 13/0243 602/41 |
| 2007/0135787 A1* | 6/2007 | Raidel ............ A61F 13/15707 604/383 |
| 2007/0185426 A1 | 8/2007 | Ambrosio et al. |
| 2007/0225663 A1 | 9/2007 | Watt et al. |
| 2007/0235038 A1* | 10/2007 | Alinsod ............ A61B 17/02 128/849 |
| 2008/0119802 A1 | 5/2008 | Riesinger |
| 2009/0227969 A1* | 9/2009 | Jaeb ............ A61M 1/0088 604/313 |
| 2014/0163491 A1 | 6/2014 | Schuessler et al. |
| 2015/0080788 A1 | 3/2015 | Blott et al. |

FOREIGN PATENT DOCUMENTS

| | | | |
|---|---|---|---|
| AU | 755496 | | 2/2002 |
| CA | 2005436 | | 6/1990 |
| DE | 26 40 413 A1 | | 3/1978 |
| DE | 43 06 478 A1 | | 9/1994 |
| DE | 295 04 378 U1 | | 10/1995 |
| EP | 0100148 A1 | | 2/1984 |
| EP | 0117632 A2 | | 9/1984 |
| EP | 0161865 A2 | | 11/1985 |
| EP | 0358302 A2 | | 3/1990 |
| EP | 1018967 B1 | | 8/2004 |
| EP | 2195069 A1 | | 6/2010 |
| EP | 2361641 A1 | | 8/2011 |
| GB | 692578 | | 6/1953 |
| GB | 2074029 A | * 10/1981 | ............ A61L 15/24 |
| GB | 2 195 255 A | | 4/1988 |
| GB | 2 197 789 A | | 6/1988 |
| GB | 2 220 357 A | | 1/1990 |
| GB | 2 235 877 A | | 3/1991 |
| GB | 2 329 127 B | | 3/1999 |
| GB | 2 333 965 A | | 8/1999 |
| JP | 4129536 | | 4/1992 |
| SG | 71559 | | 4/2002 |
| WO | 80/02182 | | 10/1980 |
| WO | 87/04626 | | 8/1987 |
| WO | 90/010424 | | 9/1990 |
| WO | 93/09727 | | 5/1993 |
| WO | 94/020041 | | 9/1994 |
| WO | 96/05873 | | 2/1996 |
| WO | 97/18007 | | 5/1997 |
| WO | 99/13793 | | 3/1999 |
| WO | 2007092405 A2 | | 8/2007 |
| WO | WO2007092405 A2 | | 8/2007 |
| WO | 2008041926 A1 | | 4/2008 |
| WO | 2008091521 | | 7/2008 |
| WO | WO2008091521 A2 | | 7/2008 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, ŽMaksimović, Đ. Radak, and P. Peška, "Vacuum Therapy in the Treatment of Peripheral Blood Vessels," Timok Medical Journal 11 (1986), pp. 161-164 (certified translation).

(56) References Cited

OTHER PUBLICATIONS

F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
European Examination Report corresponding to EP09792603.4, dated Dec. 15, 2016.
Extended European Search Report for corresponding Application No. 181626177, dated Jul. 16, 2018.

\* cited by examiner

MULTI-LAYER DRESSINGS, SYSTEMS, AND METHODS FOR APPLYING REDUCED PRESSURE AT A TISSUE SITE

RELATED APPLICATIONS

This application is a continuation of U.S. Non-Provisional Application Ser. No. 12/560,777, filed 16 Sep. 2009, which claims the benefit, under 35 U.S.C. § 119(e), of the filing of U.S. Provisional Patent Application Ser. No. 61/098,000, entitled "Multi-Layer Dressing, System, and Method For Applying Reduced Pressure at a Tissue Site," filed 18 Sep. 2008, and U.S. Provisional Patent Application Ser. No. 61/098,015, entitled "Laminar Dressing, System, and Method For Applying Reduced Pressure at a Tissue Site," filed 18 Sep. 2008. These applications are incorporated herein by reference for all purposes.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing, and increased formulation of granulation tissue.

Reduced-pressure treatment systems are often applied to large, highly exudating wounds present on patients undergoing acute or chronic care, as well as other severe wounds that are not readily susceptible to healing without application of reduced pressure. Low-severity wounds that are smaller in volume and produce less exudate have generally been treated using advanced dressings instead of reduced-pressure treatment.

BRIEF SUMMARY

Shortcomings with certain aspects of wound care systems and dressings are addressed by the present disclosure as shown and described in a variety of illustrative, non-limiting embodiments herein. According to an illustrative embodiment, a dressing for applying reduced pressure at a tissue site includes a dressing material for transferring the reduced pressure to the tissue site and for receiving liquid from the tissue site. The dressing material includes a tissue-interface layer for contacting the tissue site, the tissue-interface layer being a hydrophobic layer; a manifold for distributing reduced pressure, the manifold being a hydrophobic layer; and a first absorbent layer for absorbing liquid from the tissue site via the tissue-interface layer and the manifold. The manifold may be disposed between the tissue-interface layer and the first absorbent layer. The dressing may further include a drape covering at least a portion of the dressing material.

According to another illustrative, non-limiting embodiment, a system for applying a reduced pressure at a tissue site includes a reduced-pressure source for supplying reduced pressure, a reduced-pressure delivery conduit for transferring reduced pressure, a dressing material, and a drape covering at least a portion of the dressing material. The dressing material is in fluid communication with the reduced-pressure source via the reduced-pressure delivery conduit. The dressing material delivers reduced pressure to the tissue site and receives liquid from the tissue site. The dressing material includes a tissue-interface layer adapted to contact the tissue site, which is a hydrophobic layer; a manifold, which is a hydrophobic layer, for distributing reduced pressure; and a first absorbent layer for absorbing liquid from the tissue site via the tissue-interface layer and the manifold. The manifold may be disposed between the tissue-interface layer and the first absorbent layer.

According to another illustrative, non-limiting embodiment, a method for applying reduced pressure at a tissue site includes the steps of applying a dressing material to the tissue site, covering at least a portion of the dressing material with a drape, and supplying reduced pressure to the dressing material. The dressing material transfers reduced pressure to the tissue site and receives liquid from the tissue site. The dressing material includes a tissue-interface layer, which is a hydrophobic layer, for contacting the tissue site; a manifold, which is a hydrophobic layer, for distributing reduced pressure; and a first absorbent layer for absorbing liquid from the tissue site via the tissue-interface layer and the manifold. The manifold is disposed between the tissue-interface layer and the first absorbent layer.

According to another illustrative, non-limiting embodiment, a method of manufacturing a dressing for applying a reduced pressure at a tissue site includes the steps of providing a tissue-interface layer, which is a hydrophobic layer; providing a manifold having a tissue-facing side; coupling at least a portion of the tissue-facing side of the manifold to the tissue-interface layer; and providing a first absorbent layer having a tissue-facing side and that absorbs liquid. The manifold is a hydrophobic layer that distributes reduced pressure. The method of manufacturing may further include the steps of coupling at least a portion of the tissue-facing side of the first absorbent layer to the manifold. The method may also include providing a second absorbent layer having a tissue-facing side. The second absorbent layer includes a hydrophilic layer for absorbing liquid from the tissue site via the tissue-interface layer, the manifold, and the first absorbent layer. The method may also include coupling at least a portion of the tissue-facing side of the second absorbent layer to the first absorbent layer.

According to still another illustrative, non-limiting embodiment, a reduced-pressure wound dressing includes a non-adherent hydrophobic layer having a first side and a second, tissue-facing side; a porous, hydrophobic manifold layer, having a first side and a second, tissue-facing side; a quick-absorbing hydrophilic layer having a first side and a second, tissue-facing side; a fluid-storage layer having a first side and a second, tissue-facing side; and a sealing member having a first side and a second, tissue-facing side. The second, tissue-facing side of the porous, hydrophobic manifold layer is adjacent to the first side of the non-adherent hydrophobic layer. The second, tissue-facing side of the quick-absorbing hydrophilic layer is adjacent to the first side of the porous, hydrophobic manifold layer. The second, tissue-facing side of the fluid-storage layer is adjacent to the first side of the quick-absorbing hydrophilic layer. The second, tissue-facing side of the sealing member is adjacent to the first side of the fluid-storage layer.

In yet another embodiment, provided is a dressing for treating a tissue site including a manifold, a first layer, and a second layer. The manifold is adapted to be positioned at the tissue site, the manifold being fluid permeable and substantially hydrophobic. The first layer is adapted to receive fluid communicated from the tissue site through the manifold, the manifold adapted to be disposed between the tissue site and the first layer. The second layer is positioned proximate the first layer, the first layer adapted to be disposed between the manifold and the second layer, wherein the second layer is more hydrophilic than the first layer so that the second layer may pull fluid from the first layer.

In yet another embodiment, provided is a system for treating a tissue site with reduced pressure including a dressing adapted to deliver reduced pressure to the tissue site and to receive fluid from the tissue site. The dressing includes a first layer, a second layer, a third layer, and a fourth layer. The first layer is adapted to be positioned in contact with the tissue site, the first layer being a hydrophobic layer. The second layer is adapted to be positioned proximate the first layer and to distribute reduced pressure to the tissue site, the first layer adapted to be positioned between the tissue site and the second layer. The third layer is adapted to receive fluid communicated from the tissue site through the first layer and the second layer, the second layer disposed between the first layer and the third layer. The fourth layer is positioned proximate to the third layer, the fourth layer being more hydrophilic than the third layer so that the fourth layer may pull fluid from the third layer.

In yet another embodiment, provided is a dressing for treating a tissue site including a tissue-interface layer, a first layer, and a second layer. The tissue-interface layer is adapted to be positioned in contact with the tissue site. The first layer is positioned proximate the tissue-interface layer. The second layer is positioned proximate the first layer, the first layer disposed between the tissue-interface layer and the second layer, wherein the second layer is more hydrophilic than the first layer so that the second layer may pull fluid from the first layer and the tissue site.

In yet another embodiment, provided is a dressing adapted to receive fluid from a tissue site, the dressing material having a thickness, wherein the dressing is increasingly hydrophilic with increasing distance through the thickness of the dressing.

Other features and advantages of the illustrative embodiments will become apparent with reference to the drawings and detailed description that follow.

DETAILED DESCRIPTION

In the following detailed description, reference is made to the accompanying drawings, forming a part hereof, that depict illustrative embodiments of practicing the subject matter of the present disclosure. These embodiments are sufficiently described to enable those skilled in the art to practice the disclosed subject matter. Other embodiments may be utilized and logical, structural, mechanical, electrical, and chemical changes may be made without departing from the scope of this disclosure. To avoid detail not necessary to enable those skilled in the art to practice the disclosed subject matter, the description may omit certain information known to those skilled in the art. The following detailed description is, therefore, not to be taken in a limiting sense, the scope of the present disclosure being defined only by the appended claims.

Figure 1:
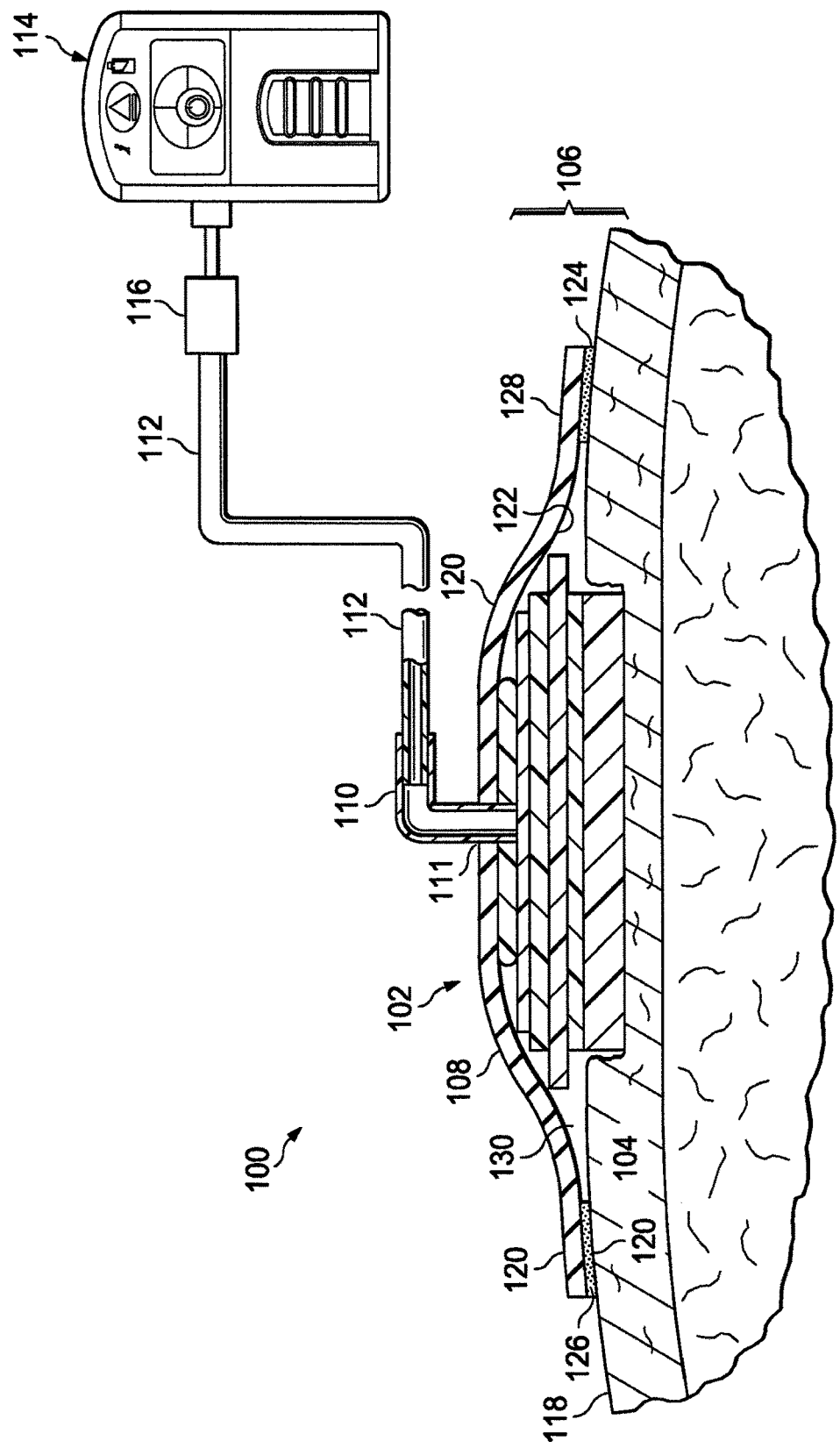
FIG. 1 is a diagram, with a portion in cross section, of an illustrative, non-limiting embodiment of a system for applying reduced pressure at a tissue site.

Referring now primarily to FIG. 1, an illustrative reduced-pressure treatment system 100, which includes a dressing 102 and which applies reduced pressure to a tissue site 104, is presented. The dressing 102 includes a dressing material 106. The dressing material 106 may include any number of layers or components and a number of illustrative, non-limiting examples will be provided herein. Unless otherwise indicated, as used herein, "or" does not require mutual exclusivity. The dressing material 106 may include one or more laminar layers. The dressing 102 may further include a sealing member 108 and a reduced-pressure connector 110, reduced-pressure interface, or connection member.

The dressing material 106 serves as a manifold for distributing reduced pressure. The term "manifold" as used herein generally refers to a substance or structure that is provided to assist in applying reduced pressure to, delivering fluids to, or removing fluids from a tissue site. The manifold typically includes a plurality of flow channels or pathways to improve distribution of fluids provided to and removed from the tissue site. The dressing material 106 that serves as a manifold may include a number of layers as will be described further below.

The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. While the tissue site 104 may include a wound, diseased tissue, or defective tissue, the tissue site 104 may also be healthy tissue that is not wounded, diseased, or defective.

The application of reduced pressure to the tissue site 104 may be used to promote the drainage of exudate and other liquids from the tissue site 104, as well as to stimulate the growth of additional tissue. In the case in which the tissue site 104 is a wound site, the growth of granulation tissue and removal of exudates and bacteria promotes healing of the wound. The application of reduced pressure to non-wounded or non-defective tissue, including healthy tissue, may be used to promote the growth of tissue that may be harvested and transplanted to another tissue location.

As used herein, "reduced pressure" generally refers to a pressure less than the ambient pressure at a tissue site 104 that is being subjected to treatment. In most cases, this reduced pressure will be less than the atmospheric pressure at which the patient is located. Alternatively, the reduced pressure may be less than a hydrostatic pressure at the tissue site 104. Unless otherwise indicated, values of pressure stated herein are gauge pressures. The reduced pressure delivered may be static or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The reduced pressure is provided to the reduced-pressure connector 110 by a reduced-pressure delivery conduit 112. The reduced-pressure delivery conduit 112 receives reduced pressure from a reduced-pressure source 114. The reduced-pressure source 114 may be any device or subsystem for supplying a reduced pressure, including but not limited to a manually operated pump, a powered vacuum pump, a wall vacuum source, etc. While the amount and nature of reduced pressure applied to a tissue site will typically vary according to the application, the reduced pressure will typically be between −5 mm Hg and −500 mm Hg and more typically between −100 mm Hg and −200 mm Hg. In one illustrative embodiment, the reduced-pressure source 114 may be a battery-driven vacuum pump. In one illustrative example, the pump uses low amounts of power and is capable of operating for an extended period of time on a single charge of the battery.

One or more devices may be fluidly coupled between the reduced-pressure connector 110 and the reduced-pressure source 114. For example, representative device 116 is shown fluidly coupled on a portion of the reduced-pressure delivery conduit 112. The representative device 116 may be a fluid reservoir, or collection member, to hold exudates and other fluids removed. Other illustrative, non-limiting examples of devices 116 that may be included on the reduced-pressure delivery conduit 112 or otherwise fluidly coupled to the reduced-pressure delivery conduit 112 include the following non-limiting examples: a pressure-feedback device, a volume detection system, a blood detection system, an infection detection system, a flow monitoring system, a temperature monitoring system, etc. Some of these devices may be formed integrally to the reduced-pressure source 114 or other aspects of the system 100.

The dressing 102 is adapted to contact or cover the tissue site 104 that is to be treated. As used herein, the term "cover" includes partially or fully covering. Also, a first object that covers a second object may directly or indirectly touch the second object, or may not touch the second object at all.

The dressing material 106 is covered fully or partially by the sealing member 108, or drape. The sealing member 108 may be any material that provides a fluid seal over the dressing material 106 and a portion of a patient's epidermis 118. The sealing member 108 may, for example, be an impermeable or semi-permeable, elastomeric material. "Elastomeric" means having the properties of an elastomer, such as a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of sealing member materials include a silicone drape, 3M Tegaderm® drape, acrylic drape such as one available from Avery Dennison, or an incise drape.

The sealing member 108 may be provided in "sheet" form, or in a pourable or sprayable form that is applied over the dressing material 106 after placement of the dressing material 106 in contact with the tissue site 104. Ins some embodiments, sealing member 108 may include a device that is placed over the dressing material 106 and the tissue site 104 to provide sealing functionality, including but not limited to, a suction cup, a molded cast, and a bell jar. The sealing member 108 has a first side 120 and a second, tissue-facing side 122.

An attachment device 124 may be used to hold the sealing member 108 against the patient's epidermis 118 or another layer, such as a gasket or additional sealing member. The attachment device 124 may take numerous forms. For example, the attachment device 124 may be a medically acceptable, pressure-sensitive adhesive 126 that extends about a periphery, or perimeter 128, of the sealing member 108.

In one embodiment, the sealing member 108 is configured to provide a sealed connection with the patient's epidermis 118 (or other tissue surrounding the dressing material 106) and the tissue site 104. The sealed connection may be provided by the adhesive 126 positioned along the perimeter 128 of the sealing member 108, or on any portion of the sealing member 108, to secure the sealing member 108 to the dressing material 106 or the tissue surrounding the tissue site 104. The adhesive 126 may be pre-positioned on the sealing member 108 or may be sprayed or otherwise applied to the sealing member 108 immediately prior to installing the sealing member 108. Prior to the application of the sealing member 108 to the tissue site 104, the adhesive 126 may also be covered by an adhesive support layer or removable backing. The adhesive support layer may provide rigidity to the sealing member 108 prior to application and may also aid in the actual application of the sealing member 108 onto the tissue site 104 or tissue near the tissue site 104. The adhesive support layer may be peeled off or otherwise removed before applying the sealing member 108.

The reduced-pressure connector 110 is coupled to the sealing member 108 and provides reduced pressure to an interior space 130 formed between the second, tissue-facing side 122 of the sealing member 108 and the tissue site 104. In another embodiment, the reduced-pressure delivery conduit 112 may directly couple the reduced-pressure source 114 to the dressing 102.

The reduced-pressure delivery conduit 112 may be any tube or flow path through which a gas, liquid, gel, or other fluid may flow. The possible embodiments of the reduced-pressure delivery conduit 112 are numerous, and non-limiting examples follow. The reduced-pressure delivery conduit 112 may have any cross-sectional shape, such as a circle, oval, or polygon. In addition, the reduced-pressure delivery conduit 112 may be made from any material, and may be either flexible or inflexible. In FIG. 1, the reduced-pressure delivery conduit 112 couples the reduced-pressure connector 110 to the representative device 116, and couples the representative device 116 to the reduced-pressure source 114. However, reduced-pressure delivery conduit 112 may directly couple reduced-pressure source 114 to the dressing 102. Also, the reduced-pressure delivery conduit 112 may include one or more paths or lumens through which fluid may flow. For example, the reduced-pressure delivery conduit 112 may include two lumens with one lumen used to administer pressure measurements to determine the amount of reduced pressure being applied at the tissue site 104. The other lumen may be used to deliver fluids, such as air, antibacterial agents, antiviral agents, cell-growth promotion agents, irrigation fluids, or other chemically active agents, to the tissue site 104. The fluid source from which these fluids originate is not shown in FIG. 1.

The reduced-pressure connector 110 permits the passage of a fluid (such as exudates, air, etc.) from the dressing material 106 to reduced-pressure delivery conduit 112, and vice versa. In another illustrative embodiment (not shown), the reduced-pressure treatment system 100 does not include the reduced-pressure connector 110. In this illustrative embodiment, the reduced-pressure delivery conduit 112 may be inserted directly into the sealing member 108 or the dressing material 106 such that an end of the reduced-pressure delivery conduit 112 is adjacent to or in contact with the sealing member 108 or any of the dressing material 106 in a manner that allows for the delivery of reduced pressure. In the non-limiting example shown in FIG. 1, the sealing member 108 includes an aperture 111 through which the reduced-pressure connector 110 is disposed.

The reduced-pressure connector 110 may be located anywhere relative to the dressing material 106. For example, although FIG. 1 shows the reduced-pressure connector 110 and the opening or aperture 111 in the sealing member 108 through which the reduced-pressure connector 110 extends as centrally located relative to the dressing material 106, the reduced-pressure connector 110 and the opening or aperture 111 may be located adjacent to the edges of the dressing material 106 or at other locations.

In operation, the dressing 102 is deployed on the tissue site 104 and reduced pressure is delivered to the tissue site 104. More specifically, the dressing material 106 is deployed proximate the tissue site 104 where treatment is desired. The sealing member 108 is deployed over the dressing material 106 and at least a portion of the patient's epidermis 118 to form the interior space 130, or sealed space. If not already accomplished, the aperture 111 may be formed in the sealing member 108 and the reduced-pressure connector 110 applied. If not already accomplished, the reduced-pressure delivery conduit 112 is fluidly coupled to the reduced-pressure connector 110 and to the reduced-pressure source 114. The reduced-pressure source 114 is activated and reduced pressure is delivered to the tissue site 104.

Figure 2:
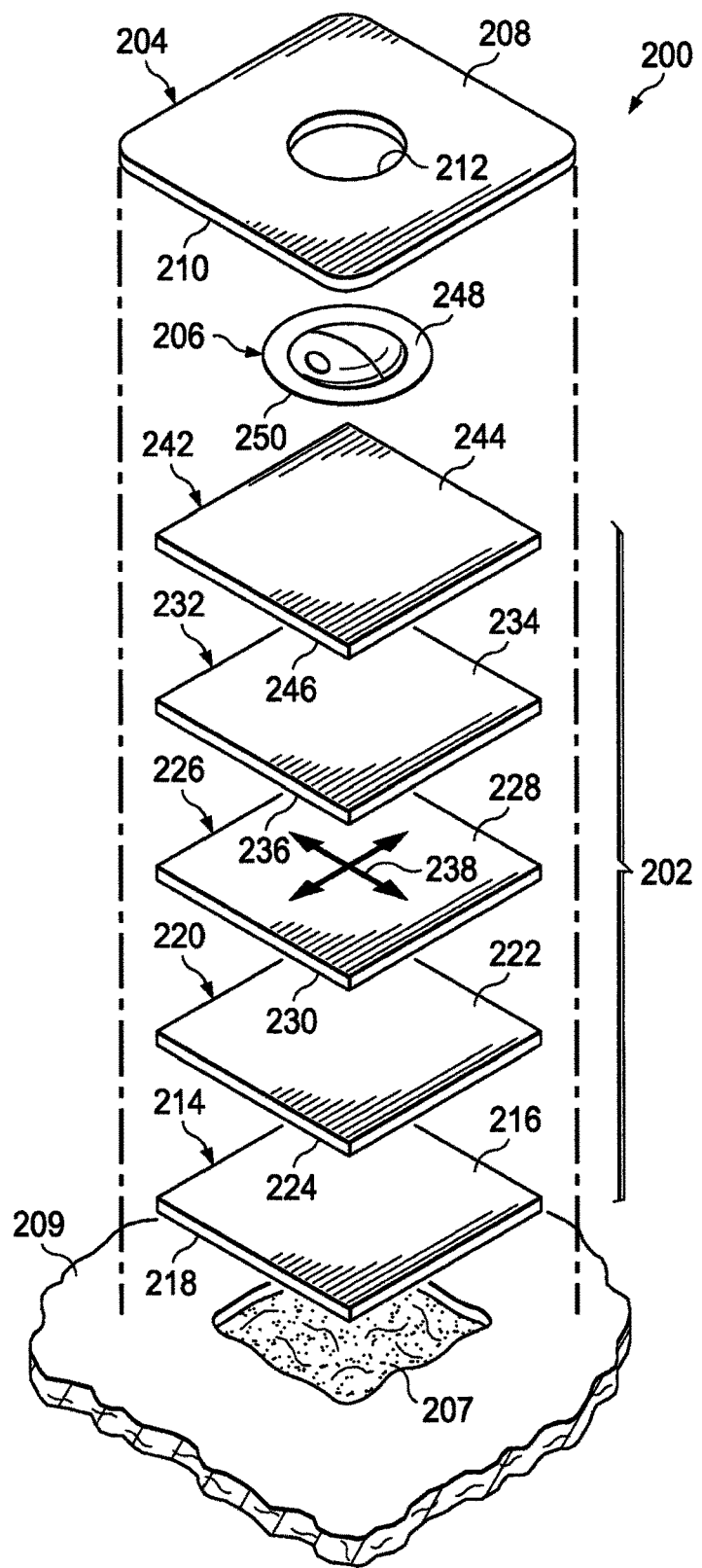
FIG. 2 is an exploded, perspective view of an illustrative, non-limiting embodiment of a dressing for applying reduced pressure at a tissue site.

Referring now primarily to FIG. 2, an exploded view of an illustrative dressing 200, which is suitable for use as dressing 102 in FIG. 1, is presented. The dressing 200 includes a dressing material 202, a sealing member 204 covering the dressing material 202, and a reduced-pressure connector 206. The reduced-pressure connector 206 may be disposed in part between the dressing material 202 and the sealing member 204. The dressing material 202 may be used to manifold, or distribute, pressure to a tissue site 207, e.g., a wound. The sealing member 204 provides a seal over the dressing material 202 and a portion of a patient's epidermis 209. The sealing member 204 has a first side 208 and a second, tissue-facing side 210. The sealing member 204 may also be formed with an aperture 212.

The dressing material 202 includes a number of components, e.g., layers or portions of material. First, a tissue-interface layer 214 has a first side 216 and a second, tissue-facing side 218. The tissue-interface layer 214 is adapted to contact the tissue site 207. In an example in which the dressing 200 is used to treat a wound, the tissue-interface layer 214 may be partially or fully in contact with the tissue site 207. The tissue site 207 may directly contact any portion of the second, tissue-facing side 218 of the tissue-interface layer 214, including the center or peripheral portions of the tissue-interface layer 214. The second, tissue-facing side 218 of the tissue-interface layer 214 may also directly contact a periwound area of the tissue site 207, which may include healthy tissue that surrounds the tissue site 207. In the illustrative embodiments, the tissue-interface layer 214, either alone or when used in conjunction with other layers, may reduce or eliminate maceration at or near the tissue site 207, including the periwound area and healthy epidermis 209 that surrounds the tissue site 207.

In an illustrative embodiment, the tissue-interface layer 214 is a hydrophobic layer. The hydrophobic characteristics of the tissue-interface layer 214 prevent the tissue-interface layer 214 from directly absorbing liquid, such as exudate, from the tissue site 207, but allow the liquid to pass through. Thus, the liquid may be drawn away from the tissue site 207 via the tissue-interface layer 214 using a reduced-pressure source, such as the reduced-pressure source 114 in FIG. 1, or may be absorbed by one or more other layers in the dressing material 202. Thus, the tissue-interface layer 214 permits the passage of liquid away from the tissue site 104, while maintaining contact with the tissue site 207.

Because the tissue-interface layer 214 does not absorb (or hold) liquid, the tissue site 207 is not exposed, or otherwise in contact, with any hydrophilic material that is substantially saturated with liquid and that could promote maceration. Also, no capillary action takes place in a direction along the surface of the tissue site 207. Thus, the hydrophobic characteristics of the tissue-interface layer 214 may also restrain or prevent the spread of liquid along an interface between the tissue site 207 and the second, tissue-facing side 218 of the tissue-interface layer 214.

The tissue-interface layer 214 may be composed of any of a variety of materials, and have a variety of structures, including materials and structures that allow fluid, e.g., liquid or gas, to pass through the tissue-interface layer 214. In one example, the tissue-interface layer 214 may be composed of or include nylon. In another example, the tissue-interface layer 214 may be composed of or include a polymer-based mesh fabric. In another example, the tissue-interface layer 214 may be composed of or include Teflon®-impregnated polyethylene. The tissue-interface layer 214 may also be composed of or include spandex or Elastane® material. The tissue-interface layer 214 may be a thin, non-adherent, hydrophobic, non-stitch layer. The tissue-interface layer 214 may function, typically under reduced-pressure, to quickly transport moisture from the tissue site 207. The tissue-interface layer 214 may be non-absorbent in nature.

The tissue-interface layer 214 may also exhibit non-adherent properties such that the tissue-interface layer 214 does not stick to or adhere to the tissue site 207. The tissue-interface layer 214 may also be stretchable, or elastic, in nature. The stretchable properties of the tissue-interface layer 214 may facilitate placement of the tissue-interface layer 214 adjacent to tissue sites and wounds having a variety of shapes, topologies, or flexibility requirements.

The tissue-interface layer 214 may be used to promote granulation at the tissue site 207 when reduced pressure is applied through the dressing 200. For example, any or all of the surfaces of the tissue-interface layer 214 may have an uneven, coarse, or jagged profile that causes microstrains and stresses at the tissue site 207 when a pressure is applied. Thus, the reduced pressure supplied may cause the tissue-interface layer 214 to create microstrain and thereby encourage granulation. The tissue-interface layer 214 may further serve as a scaffold for new cell-growth, or a scaffold material may be used in conjunction with the tissue-interface layer 214 to promote cell-growth. A scaffold is a substance or structure used to enhance or promote the growth of cells or formation of tissue, such as a three-dimensional porous structure that provides a template for cell growth.

The tissue-interface layer 214 may have any size, shape, or thickness depending on a variety of factors, such as the type of treatment being implemented or the nature of the tissue site 207. The size and shape of the tissue-interface layer 214 may be customized by a user to cover a particular portion of the tissue site 207 or nearby tissue. The tissue-interface layer 214 may also have a laminar size or thickness that is the same or different from any one of the other layers in the dressing material 202. In another example, the tissue-interface layer 214 may be thinner than any of the other layers in the dressing material 202.

The dressing material 202 also includes a manifold 220, or manifold layer or manifold member, for distributing reduced pressure from a reduced-pressure source, such as reduced-pressure source 110 in FIG. 1. The manifold 220 may also distribute liquid, such as exudate, from the tissue-interface layer 214 to other layers in the dressing material 202. The manifold 220 has a first side 222 and a second, tissue-facing side 224. The second, tissue-facing side 224 of the manifold 220 is disposed proximate the first side 216 of the tissue-interface layer 214.

The manifold 220 may be a hydrophobic, porous material that is capable of distributing reduced pressure to the tissue site 207. The manifold 220 may be made from foam, gauze, felted mat, or any other material suited to a particular biological application. The manifold 220 may include a plurality of flow channels or pathways to facilitate distribution of reduced pressure or fluids to or from the tissue site 207. In one embodiment, the manifold 220 is a porous foam and includes a plurality of interconnected cells or pores that act as flow channels. The porous foam may be a polyurethane, open-cell, reticulated foam, such as the GranuFoam® dressing available from Kinetic Concepts, Inc. of San Antonio, Tex. If an open-cell foam is used, the porosity may vary. The flow channels allow fluid communication throughout a portion of the manifold 220 having open cells. The cells and flow channels may be uniform in shape and size, or may include patterned or random variations in shape and size. Variations in the shape and size of the cells of the manifold 220 result in variations in the flow channels, and such characteristics may be used to alter the flow characteristics of fluid through the manifold 220. In one non-limiting example, the manifold 220 may be made from the same material as the tissue-interface layer 214.

A number of additional layers may be added to absorb fluid from the manifold 220 or tissue-interface layer 214. The additional layers may be absorbers. The additional layers are selected so that the farther the additional layers are located in situ from the tissue site 207, the more the layers can absorb. The additional layers thus may be increasingly hydrophilic. In the illustrative embodiment of FIG. 2, a first absorbent layer 226, which has a first side 228 and a second, tissue-facing side 230, may be included with the dressing material 202. The second, tissue-facing side 230 may be disposed proximate to the first side 222 of the manifold 220. The first absorbent layer 226 is for receiving and absorbing the liquids distributed by the manifold 220.

A second absorbent layer 232, or reservoir layer, which has a first side 234 and a second, tissue-facing side 236, may also be included with the dressing material 202. Additional absorbent layers analogous to the first absorbent layer 226 or second absorbent layer 232 may also be included in other embodiments. The second, tissue-facing side 236 of the second absorbent layer 232 may be disposed proximate the first side 228 of the first absorbent layer 226. As with other layers, the first absorbent layer 226 and second absorbent layer 232 may be coextensive or may be different sizes.

The absorbent layers 226, 232 receive and absorb liquids from the manifold 220. The manifold 220 may facilitate the migration of liquid from the tissue site 207 radially outward toward the edges of the manifold 220 so that the liquid is distributed more uniformly across either or both of the absorbent layers 226 and 232 as indicated generally by the multi-directional arrows 238 shown for reference on the first absorbent layer 226. The absorbent layers 226 and 232 will retain more liquid if the liquid is more uniformly distributed across the surface of the absorbent layers 226 and 232. Also, such distribution of the liquid from the tissue site 207 in the directions indicated by the multi-directional arrows 238 may occur with or without the presence of reduced pressure. Thus, a fuller utilization of either or both of the absorbent layers 226 and 232 may be achieved using the manifold 220 even when reduced pressure is not being applied to the dressing 200.

The manifold 220 may also act as a separator between the tissue-interface layer 214 and either or both of the absorbent layers 226 and 232. In this example, the manifold 220, reduces, restrains, or prevents liquid, such as exudate, that has been absorbed by either or both of the absorbent layers 226 and 232 from contacting either or both of the tissue-interface layer 214 or the tissue site 207. Thus, the manifold 220 may further help to prevent maceration at or near the tissue site 207.

The manifold 220 may have any size, shape, or thickness depending on a variety of factors, such as the type of treatment being implemented or the nature of the tissue site 207. For example, the thickness of the manifold 220 may be increased or decreased to optimize the effectiveness of the manifold's 220 role as a separator between the tissue-interface layer 214 and either or both of the absorbent layers 226 and 232. In applications in which the tissue site 207 releases a large amount of liquid that is absorbed by either or both of the absorbent layers 226 and 232, a relatively thicker manifold 220 may be desirable to restrain or prevent the liquid that is absorbed by either or both of the absorbent layers 226 and 232 from contacting either or both of the tissue-interface layer 214 or the tissue site 207. A relatively thinner manifold 220 may be desirable in applications in which a lower amount of liquid is present. In illustrative, non-limiting embodiments, the manifold 220 may be about 4 millimeters, 2 millimeters, or 1 millimeter thick. The manifold 220 may also have a laminar size or thickness that is the same or different from any one of the other layers in the dressing material 202.

The first absorbent layer 226 may be disposed adjacent to the manifold 220 and absorb liquid, such as exudate, from the tissue site 207 via the tissue-interface layer 214 and the manifold 220. In one example, the first absorbent layer 226 is disposed between the manifold 220 and the second absorbent layer 232.

The first absorbent layer 226 may be formed from a hydrophilic material to facilitate absorption of the liquid from the tissue site 207. In one embodiment, the first absorbent layer 226 is formed of a material that absorbs liquid from the tissue site 207 at a faster rate than the second absorbent layer 232. For example, the first absorbent layer 226 may include a fast-wicking material, such as cotton, terrycloth, paper towel material, etc. To quicken the rate at which the first absorbent layer 226 absorbs liquid from the tissue site 207, the surface area of the first absorbent layer 226 may be increased. The first absorbent layer 226 may also be made from a woven or mesh material.

In one embodiment, the fast-wicking characteristics of the first absorbent layer 226, including the first absorbent layer's 226 ability to absorb liquid at a faster rate than the second absorbent layer 232, helps to quickly draw liquid away from the tissue site 207 and toward the second absorbent layer 232, which may have a higher absorptive capacity than the first absorbent layer 226. The first absorbent layer's 226 ability to quickly draw liquid away from the tissue site 207 may prevent the accumulation of liquid at or near the tissue site 207, and therefore may help to prevent maceration at or near the tissue site 207.

The first absorbent layer 226 may have any size, shape, or thickness depending on a variety of factors, such as the type of treatment being implemented or the nature of the tissue site 207. The first absorbent layer 226 may also have a size or thickness that is the same or different from any one of the other layers in the dressing material 202.

In one embodiment, the second absorbent layer 232 absorbs liquid from the tissue site 207 via the tissue-interface layer 214, the manifold 220, and the first absorbent layer 226. In another illustrative embodiment (not shown), the dressing material 202 does not include the first absorbent layer 226, in which case the second absorbent layer 232 is the only absorbent layer present in the dressing material 202. In this embodiment, the second absorbent layer 232 absorbs liquid from the tissue site 207 via the tissue-interface layer 214 and the manifold 220. In other embodiments, more than two absorbent layers may be included.

The second absorbent layer 232 may be composed of any material capable of absorbing liquid, such as exudate, from the tissue site 207. The material from which the second absorbent layer 232 is composed is also capable of transferring reduced pressure. In one embodiment, the second absorbent layer 232 has a higher fluid storage capacity than the first absorbent layer 226. The difference in fluid storage capacity may be due to the respective materials from which absorbent layers 226 and 232 are composed. In one example, the second absorbent layer 232 may be capable of storing liquid that is 20 or more times heavier or voluminous than the dry weight or volume, respectively, of the second absorbent layer 232.

In the illustrative example of FIG. 2, the second absorbent layer 232 wicks liquid away from the first absorbent layer 226, and stores that liquid. To facilitate the second absorbent layer's 232 function of wicking liquid away from the first absorbent layer 226, the second absorbent layer 232 may be composed of a material that is more hydrophilic than the material from which the first absorbent layer 226 is composed.

In one embodiment, the second absorbent layer 232 may be composed of a hydrocolloid or hydrogel, which may be, for example, a First Water® Net2O hydrogel from First Water, Ltd. of Wiltshire, U.K. The hydrogel from which the second absorbent layer 232 is composed may also include polyethylene glycol. Further, although hydrogel infers the inclusion of water, the hydrogel from which the second absorbent layer 232 may be composed may be a dried back hydrogel polymer base, which substantially or completely lacks water.

In another illustrative example, the second absorbent layer 232 may be made from a super absorbent fiber material. The super absorbent fibers may hold onto or bond to the liquid in conjunction with a physical or chemical change to the fibers. In one non-limiting example, the super absorbent fiber may include the Super Absorbent Fiber (SAF) material from Technical Absorbents, Ltd. of Lincolnshire, UK. The fibers may thus form a fibrous material in which the fibers absorb liquid from the tissue site 207. Also, the fibers in the second absorbent layer 232 that contact the liquid may gel upon contact with the liquid, thereby trapping the liquid. Spaces or voids between the fibers may allow a reduced pressure that is applied to the dressing 200 to be transferred within and through the second absorbent layer 232. The structure of the second absorbent layer 232 that contains the fibers may be either woven or non-woven.

The second absorbent layer 232 may have any size, shape, or thickness depending on a variety of factors, such as the type of treatment being implemented or the nature of the tissue site 207. For example, the width or thickness of the second absorbent layer 232 may be increased to cause a corresponding increase in the fluid storage capacity of the second absorbent layer 232. The second absorbent layer 232 may also have a size or thickness that is the same or different from any one of the other layers in the dressing material 202.

The dressing material 202 also includes a distribution manifold 242 that is adjacent to the second absorbent layer 232. The distribution manifold 242 has a first side 244 and a second, patient-facing side 246. The second, patient-facing side 246 of the distribution manifold 242 is disposed adjacent to the first side 234 of the second absorbent layer 232. The distribution manifold 242 distributes reduced pressure to one or more layers in the dressing material 202 that are nearer the tissue site 207 and may do so more uniformly across an entire surface of the one or more layers in the dressing material 202. Because the distribution manifold 242 is disposed further away from the tissue site 207 than the absorbent layers 226 and 232, liquid, such as exudate, from the tissue site 207 does not typically reach the distribution manifold 242. In one illustrative embodiment, however, liquid may be allowed to reach the distribution manifold 242.

The distribution manifold 242 may be made from any material capable of distributing gas or liquid. In one example, the distribution manifold 242 is formed from a reticulated polyurethane foam layer or other porous manifolding material. In another example, the distribution manifold 242 may be formed from the same or similar material as the manifold 220. The distribution manifold 242 may also distribute liquid, such as exudate, from the tissue site 207 that is not absorbed by either or both of the absorbent layers 226 and 232. The distribution manifold 242 may also have any size, shape, or thickness.

Although not explicitly shown in the embodiment of FIG. 2, the dressing 200 may also include a hydrophobic filter that is capable of restraining or preventing the flow of liquid, such as exudate from the tissue site 207, from reaching the reduced-pressure connector 206 or a reduced-pressure conduit that may be connected to the dressing 200. By preventing liquid from reaching the reduced-pressure conduit, the hydrophobic filter also prevents the liquid from reaching a reduced-pressure source, such as reduced-pressure source 114 in FIG. 1, which may be connected to the reduced-pressure delivery conduit.

In one illustrative embodiment, the hydrophobic filter is disposed adjacent to the distribution manifold 242. The second, tissue-facing side of the hydrophobic filter may abut the first side 244 of the distribution manifold 242 and the first side of the hydrophobic filter may abut the second, tissue-facing side 210 of the sealing member 204 or the reduced-pressure connector 206. As used herein, the term "abut" includes both fully and partially abutting.

The hydrophobic filter may also restrict or prevent the passage of reduced pressure to the tissue site 207 when the hydrophobic filter becomes substantially saturated, clogged, blocked, or wetted with liquid from the tissue site 207. The hydrophobic filter may also prevent the passage of reduced pressure to the tissue site 207 when a layer that abuts the hydrophobic filter becomes substantially saturated with liquid. For example, if the second absorbent layer 232 abutted the hydrophobic filter in a particular embodiment, the substantial saturation of the second absorbent layer 232 with liquid may cause the hydrophobic filter to prevent the passage of reduced pressure.

The hydrophobic filter may have any size, shape, or thickness. In one example, the hydrophobic filter may be smaller than other layers in the dressing material 202 or may be larger than other layers. The hydrophobic filter may also be wider than the reduced-pressure connector 206 and an aperture 212 in the sealing member 204 so that liquid from the tissue site 207 cannot reach the reduced-pressure connector 206 or the aperture 212.

The dressing 200 may include the sealing member 204. The sealing member 204 may cover at least a portion of the dressing material 202. In this embodiment, the sealing member 204 may fully cover the dressing material 202 and may secure the dressing material 202 to the tissue site 207. The sealing member 204 may also assist in maintaining a fluid seal around a portion of the tissue site 207. The sealing member 204 may also provide a protective covering for the dressing 200. As used herein, "fluid seal," or "seal" means a seal adequate to maintain reduced pressure at a desired site given the particular reduced-pressure source involved.

In one illustrative embodiment, the sealing member 204 may be an adhesive drape. In this embodiment, the adhesion of the sealing member 204 may be due to the nature of the material with which the sealing member 204 is made, or may be due to an adhesive layer, e.g., like adhesive 126 in FIG. 1, on a surface of the sealing member 204. Any portion of the sealing member 204 may be adhesive. For example, the entire second, tissue-facing side 210 of the sealing member 204 may be adhesive. In this example, the second, tissue-facing side 210 of the sealing member 204 may adhere to at least a portion of the reduced-pressure connector 206, a portion of the tissue site 207 (or epidermis 209 around and that may be regarded as part of the tissue site 207), or any layer or component of the dressing material 202.

In another embodiment, only the peripheral portions of the second, tissue-facing side 210 of the sealing member 204 may be adhesive. In this embodiment, the peripheral portions are adjacent to the edges of the sealing member 204. The adhesive peripheral portions on the tissue-facing side of the sealing member 204 may be adapted to adhere to the tissue site 207 to secure the dressing material 202 to the tissue site 207.

In another illustrative example, the sealing member 204 may be a drape and may be designed such that the drape will not adhere to wet surfaces, but will adhere to dry surfaces. Thus, when applying such a drape, the drape will not stick to moistened gloves or hands, thereby will permit easier handling of the drape until the drape is placed on a dry tissue site, such as a dry periwound region. The sealing member 204 may have any size, shape, or thickness. In one example, the sealing member 204 may be wider or larger than any layer or components of the dressing material 202.

Reduced pressure may be applied to the dressing material 202 via the reduced-pressure connector 206 extending through the aperture 212 in the sealing member 204. In the illustrative example of FIG. 2, the aperture 212 is shown centrally located on the sealing member 204. However, the aperture 212 may be located anywhere on the sealing member 204, including a peripheral portion of the sealing member 204 that is adjacent to an edge of the sealing member 204. Although the aperture 212 is shown to be circular, it should be understood that the aperture 212 may have any shape, e.g., square, elliptical, irregular, etc. In one example, the shape of the aperture 212 is adapted to contour, or substantially coordinate, with one or more portions of the reduced-pressure connector 206.

The reduced-pressure connector 206 may provide an interface between a reduced-pressure conduit and the dressing material 202. In particular, the reduced-pressure connector 206 may be adapted to be in fluid communication, or fluidly coupled, to a reduced-pressure conduit, such as reduced-pressure delivery conduit 112 in FIG. 1. The reduced-pressure conduit transfers reduced pressure to the dressing 200 or the tissue site 207 via the reduced-pressure connector 206.

The reduced-pressure connector 206 may be a connector pad that is adapted to abut the aperture 212. In particular, the reduced-pressure connector 206 may be adapted to be partially disposed within the aperture 212. Although the reduced-pressure connector 206 is shown to have a low profile dome shape, the reduced-pressure connector 206 may have any shape. The low profile of the reduced-pressure connector 206 may help to keep the dressing 200 compact and convenient for use by a user. The reduced-pressure connector 206 may includes a flanging portion 248, which is disposed around the periphery of the reduced-pressure connector 206. In the example of FIG. 2, the tissue-facing side of the edge defining the aperture 212 may be adapted to adhere to the flanging portion 248 such that the reduced-pressure connector 206 is secured to at least one layer or component of the dressing material 202.

Although not shown in FIG. 2, in one embodiment the dressing material 202 may include an odor filter. The odor filter may retrain or prevent odor from exiting the dressing 200. The odor filter may be a carbon odor filter, which may include charcoal. For example, the odor filter may be a charcoal cloth. The odor filter may be positioned anywhere in the dressing material 202. For example, in the embodiment in which the dressing 200 includes a hydrophobic filter, the odor filter may be disposed adjacent to a first, drape-facing side of the hydrophobic filter. When in use, the odor filter may also abut the first, drape-facing side of the hydrophobic filter.

Although the sealing member 204, the distribution manifold 242, the absorbent layers 226 and 232, the manifold 220, and the tissue-interface layer 214 are each shown to have a square shape, each of these components, as well as other layers disclosed herein with respect to other embodiments, may have any shape as desired or required to provide adequate reduced-pressure therapy to the tissue site 207. For example, these components and layers may have any polygonal shape, a rectangular shape, a circular shape, an oval shape, an irregular shape, a customized shape, etc. The shape of these components and layers may also be customized to contour the tissue site 207.

The layers forming the dressing material 202 may be manufactured in the order shown in FIG. 2 or any other order. As previously noted, one or more layers may be omitted. The layers forming the dressing material may be bonded to form an integrated member or remain as separate stacked members. As used herein, "bonding" may include coupling items using any known technique, including without limitation welding (e.g., ultrasonic or RF welding), bonding, adhesives, cements, material attraction, etc. The layers may be bonded an then cut.

Figure 3:
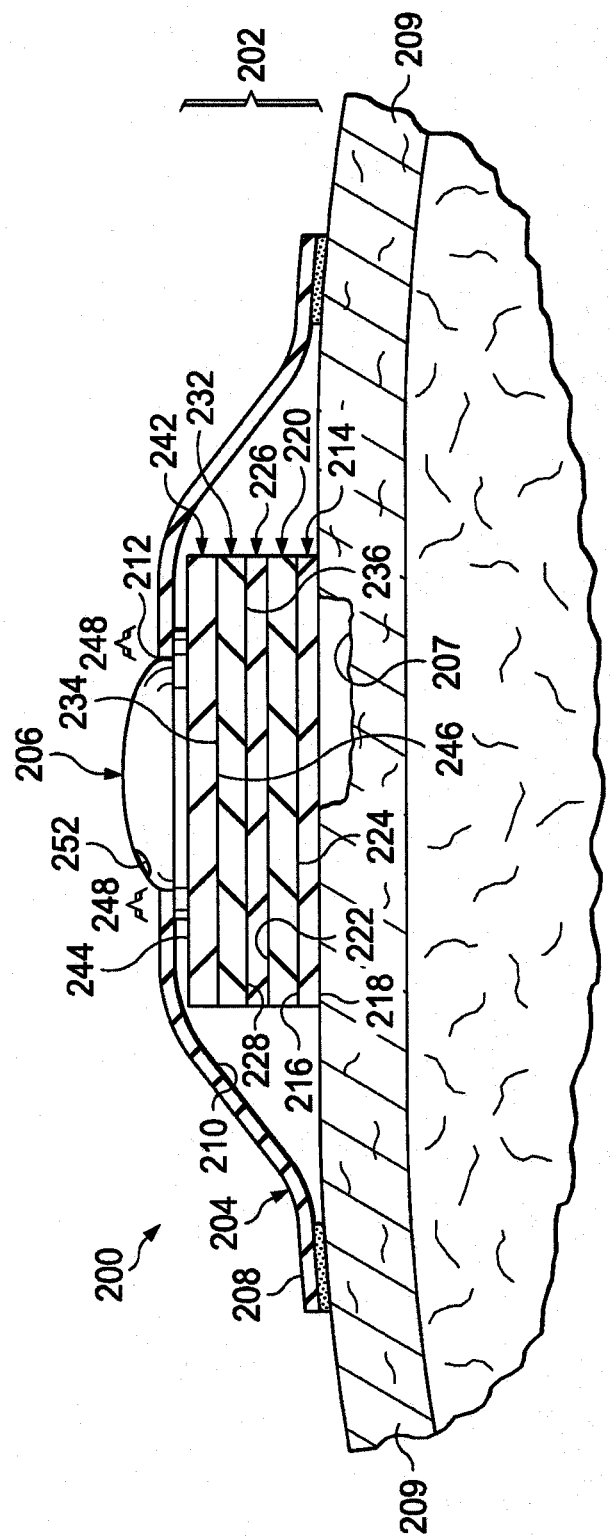
FIG. 3 is a schematic, cross-sectional view of the dressing of FIG. 2 deployed for use in applying reduced pressure at a tissue site.

Referring now primarily to FIG. 3, the illustrative dressing 200 of FIG. 2 is shown assembled and deployed to treat the tissue site 207. The second, tissue-facing side 218 of the tissue-interface layer 214 is shown abutting the tissue site 207, which includes a wound and a portion of the epidermis 209 in this illustration. The first side 244 (or at least a portion) of the distribution manifold 242 may abut the sealing member 204.

The second, tissue-facing side 250 of the reduced-pressure connector 206 abuts the distribution manifold 242. Also, a portion of the reduced-pressure connector 206 is shown to protrude from the aperture 212 in the sealing member 204. The flanging portion 248 of the reduced-pressure connector 206 is sandwiched between the sealing member 204 and the distribution manifold 242. The sealing member 204 helps secure the reduced-pressure connector 206 relative to at least one component or layer in the dressing material 202, such as the distribution manifold 242.

Although empty space is shown between the peripheral portions of the sealing member 204 and the tissue site 207, in one example when under reduced pressure, little or no space is present between the peripheral portions of the sealing member 204 and the tissue site 207. Also, although the tissue-interface layer 214, the manifold 220, the absorbent layers 226 and 232, and the distribution manifold 242 are shown to have a uniform width, the width of any combination of these layers may vary from one another. Similarly, the thickness of any combination of these layers may be uniform or may vary from one another. In one example, the second absorbent layer 232 is thicker than the first absorbent layer 226.

When reduced pressure from a reduced-pressure delivery conduit, such as reduced-pressure delivery conduit 112 in FIG. 1, passes to the dressing 200, the reduced pressure is applied to the tissue site 207 via the dressing material 202 and the reduced-pressure connector 206. The reduced-pressure delivery conduit may be connected to the reduced-pressure connector 206 using a recess 252 in the reduced-pressure connector 206, an attachment base, or other device. Under reduced pressure, the second absorbent layer 232 (or reservoir layer) may absorb liquid from the tissue site 207 via the tissue-interface layer 214, the manifold 220, and the first absorbent layer 226.

In one embodiment, a method of using the dressing 200 includes deploying the dressing material 202 adjacent the tissue site 207. The method may also include covering at least a portion of the dressing material 202 with the sealing member 204, and applying reduced pressure.

In one illustrative example of the operation of the dressing 200 as part of a reduced-pressure system, reduced pressure is delivered to the dressing 200 and causes liquid, such as exudate, to be drawn away from the tissue site 207. The liquid passes through the tissue-interface layer 214 while the tissue-interface layer 214 maintains substantial contact with the tissue site 207. The hydrophobic nature of the tissue-interface layer 214 prevents liquid from being directly absorbed (or held) by the tissue-interface layer 214 and remaining near the surface of the tissue site 207. In addition, the fast-wicking characteristics of the first absorbent layer 226 allows the first absorbent layer 226 to absorb liquid via the manifold 220 such that the liquid is drawn quickly away from the tissue site 207. Upon being wicked by the first absorbent layer 226, the second absorbent layer 232 may receive and store the liquid. The manifold 220 provides an intervening layer that prevents liquid that is absorbed by either or both of the absorbent layers 226 and 232 from returning to the tissue site 207. In this example of the operation of the dressing 200, maceration of the epidermis 209 near the tissue site 207, is reduced or prevented due to the liquid being quickly drawn away from the tissue site 207 and stored at a location that has little or no effect on the tissue site 207.

One aspect upon which the operation of the dressing 200 may be implemented is that one or more faster-absorbing, lower-storage-capacity absorbing layers, such as the first absorbent layer 226, may be positioned closer to the tissue site 207 than slower-absorbing, higher-storage-capacity absorbing layers, such as the second absorbent layer 232. Using this approach, liquid may be drawn away from the tissue site 207 before the liquid is able to damage the surface at or near the tissue site 207, while also providing a storage layer for this liquid that has a large storage capacity. The tissue-interface layer 214 or hydrophobic layers may be disposed between the absorbent layers 226 and 232 and the tissue site 207. Such a hydrophobic layer help keep liquids away from the tissue site 207. Due, at least in part, to the uptake of liquid by the absorbent layers 226 and 232, these hydrophobic layers also reduce or prevent the lateral spread of the liquid along the interface between the tissue-interface layer 214 and the surface of the tissue site 207, and thereby further prevents or reduces maceration of the tissue at or near the tissue site 207.

The illustrative dressings and systems herein include a dressing material adapted to transfer reduced pressure to a tissue site and that may store liquids and help avoid maceration. The illustrative embodiments provide numerous non-limiting examples of materials and non-limiting examples of layer configurations that may be included in the dressing material. Moreover, each of the layers described herein may be used in any combination with one another. For example, in each of the figures and examples showing or describing a non-limiting configuration of the dressing material, any one or more of the shown or described layers or components may be excluded, any one or more layers or components from the same or different example or figures may be added, or any one or more layers or components from the same or different example or figure may substitute another layer or component shown in the example or figure. In addition, the order, size, thickness, position, and other characteristics of the layers or components in each of the described layer configurations in the examples and figures may be altered.

According to one illustrative embodiment, a dressing material has a plurality of channel walls that form a plurality of channels. The plurality of channels may be parallel to one another. In another illustrative embodiment, the channels may be slanted relative to a skin surface at the tissue site. The plurality of channels may form an acute angle with the skin surface at the tissue site.

According to one illustrative embodiment, a wound dressing for use with a reduced-pressure treatment system includes at least one laminar layer having a first side and a second, tissue-facing side. The laminar layer includes a plurality of channel walls forming a plurality of channels; wherein the channel walls are gas permeable and liquid impermeable; wherein the channels are angled with an angle alpha ($\alpha$) to a surface on the second, tissue-facing side of the laminar layer; and wherein the angle alpha ($\alpha$) is an acute angle. The walls may be gas permeable and liquid impermeable.

According to one illustrative embodiment, a reduced-pressure wound dressing includes a non-adherent hydrophobic layer having a first side and a second, tissue-facing side; a porous, hydrophobic manifold layer, having a first side and a second, tissue-facing side; a quick-absorbing hydrophilic layer having a first side and a second, tissue-facing side; a fluid-storage layer having a first side and a second, tissue-facing side; and a sealing member having a first side and a second, tissue-facing side. The second, tissue-facing side of the porous, hydrophobic manifold layer is adjacent to the first side of the non-adherent hydrophobic layer. The second, tissue-facing side of the quick-absorbing hydrophilic layer is adjacent to the first side of the porous, hydrophobic manifold layer. The second, tissue-facing side of the fluid-storage layer is adjacent to the first side of the quick-absorbing hydrophilic layer. The second, tissue-facing side of the sealing member is adjacent to the first side of the fluid-storage layer.

Various changes, substitutions, permutations, and alterations can be made to the illustrative embodiments described herein without departing from the scope of this disclosure as defined by the appended claims. Any feature that is described in a connection to any one embodiment may also be applicable to any other embodiment.

I claim:

1. A dressing for treating a tissue site, comprising:
a tissue-interface layer adapted to be positioned in contact with the tissue site, the tissue-interface layer being non-adherent on a tissue-facing side;
a manifold adapted to be positioned at the tissue site, the manifold being fluid permeable and substantially hydrophobic, the manifold further adapted to separate liquid from the tissue interface layer and to migrate the liquid radially outward toward edges of the manifold such that the liquid is uniformly distributed across the manifold, the tissue-interface layer adapted to be positioned between the tissue site and the manifold;
a first layer adapted to receive fluid communicated from the tissue site through the manifold, the manifold adapted to be disposed between the tissue site and the first layer;
a second layer positioned proximate the first layer, the first layer disposed between the manifold and the second layer, wherein the second layer is more hydrophilic than the first layer so that the second layer may pull fluid from the first layer; and
a foam distribution manifold layer adjacent the second layer.

2. The dressing of claim 1, wherein the tissue-interface layer is hydrophobic, and wherein a tissue-facing side of the manifold abuts the tissue-interface layer.

3. The dressing of claim 1, wherein the tissue-interface layer is stretchable.

4. The dressing of claim 1, further comprising a drape adapted to cover at least a portion of the dressing, the drape having an adhesive on a tissue-facing side of the drape.

5. The dressing of claim 1, wherein the tissue-interface layer comprises a polymer-based mesh fabric.

6. The dressing of claim 1, wherein the tissue-interface layer comprises a polytetrafluoroethylene-impregnated polyethylene.

7. The dressing of claim 1, wherein the first layer comprises a hydrogel absorbent layer.

8. The dressing of claim 1, wherein the first layer comprises a plurality of fibers adapted to absorb fluid from the tissue site.

9. The dressing of claim 8, wherein at least a portion of the plurality of fibers gel when contacting fluid from the tissue site.

10. The dressing of claim 1, wherein the manifold includes a plurality of interconnected cells to form a porous foam.

11. The dressing of claim 1, further comprising:
a drape adapted to cover at least a portion of the dressing, the drape having an adhesive on a tissue-facing side of the drape,
wherein the second layer is adapted to be disposed between the drape and the first layer, and wherein a tissue-facing side of the second layer abuts the first layer.

12. The dressing of claim 1, wherein the second layer absorbs fluid at a slower rate than the first layer.

13. The dressing of claim 1, wherein the second layer has a higher fluid storage capacity than the first layer.

14. The dressing of claim 1, further comprising a tubing connector, the tubing connector adapted to be coupled to the foam distribution manifold layer.

15. The dressing of claim 1, wherein the tissue-facing side of the tissue-interface layer has a coarse texture.

16. A system for treating a tissue site with reduced pressure, comprising:
a dressing adapted to deliver reduced pressure to the tissue site and to receive fluid from the tissue site, comprising:
a first layer adapted to be positioned in contact with the tissue site, the first layer being non-adherent on a tissue-facing side and hydrophobic,
a second layer adapted to be positioned proximate the first layer and to distribute reduced pressure to the tissue site, the second layer further adapted to separate liquid from the first layer and to migrate the liquid radially outward toward edges of the second layer such that the liquid is uniformly distributed across the second layer, the first layer adapted to be positioned between the tissue site and the second layer,
a third layer adapted to receive fluid communicated from the tissue site through the first layer and the second layer, the second layer disposed between the first layer and the third layer,
a fourth layer positioned proximate to the third layer, the fourth layer being more hydrophilic than the third layer so that the fourth layer may pull fluid from the third layer, and
a foam distribution manifold layer adjacent the fourth layer.

17. The system of claim 16, further comprising a reduced-pressure source adapted to supply reduced pressure to the dressing.

18. The system of claim 17, further comprising a reduced-pressure delivery conduit, the reduced-pressure delivery conduit fluidly coupled to the reduced-pressure source and the dressing.

19. The system of claim 16, wherein the first layer comprises a polymer-based mesh fabric.

20. The system of claim 16, wherein the first layer comprises polytetrafluoroethylene-impregnated polyethylene.

21. The system of claim 16, wherein the third layer comprises a hydrogel absorbent layer.

22. The system of claim 16, further comprising a sealing member adapted to cover at least a portion of the dressing, wherein the fourth layer is adapted to be disposed between the third layer and the sealing member, and wherein a tissue-facing side of the fourth layer abuts the third layer.

23. The system of claim 16, wherein the third layer comprises a plurality of fibers adapted to absorb fluid from the tissue site, and wherein at least a portion of the plurality of fibers gel when the fibers contact fluid from the tissue site.

24. The system of claim 16, wherein the fourth layer is a hydrophilic absorbent layer.

25. The system of claim 16, wherein the second layer includes a plurality of interconnected cells adapted to form a porous foam that is fluid permeable.

26. The system of claim 16, wherein the fourth layer is adapted to absorb fluid at a slower rate than the third layer.

27. The system of claim 16, wherein the fourth layer is thicker than the third layer.

28. The system of claim 16, wherein the fourth layer has a higher fluid storage capacity than the third layer.

29. The system of claim 16, wherein the foam distribution manifold layer is adapted to distribute reduced pressure.

30. The system of claim 29, wherein a tissue-facing side of the foam distribution manifold layer abuts the fourth layer, and wherein the foam distribution manifold layer comprises a reticulated polyurethane foam.

31. The system of claim 16, further comprising a tubing connector, the tubing connector adapted to be coupled to the foam distribution manifold layer.

32. The dressing of claim 16, wherein the tissue-facing side of the first layer has a coarse texture.

* * * * *